United States Patent
Walker et al.

(10) Patent No.: US 6,406,180 B1
(45) Date of Patent: Jun. 18, 2002

(54) AMBIENT AIR TEMPERATURE AND/OR HUMIDITY SENSOR

(75) Inventors: Jeffery C. Walker; David K. Deedman; Nigel P. Fleming; Brian W. Oughton, all of Essex; Iain D. Sandoe; Paul M. Wilton, both of Hampshire, all of (GB)

(73) Assignee: BAE Systems (Defence Systems) Limited, Farnborough (GB)

( * ) Notice: Subject to any disclaimer, the term of this patent is extended or adjusted under 35 U.S.C. 154(b) by 0 days.

(21) Appl. No.: 09/457,523

(22) Filed: Dec. 9, 1999

(30) Foreign Application Priority Data

Dec. 11, 1998 (GB) ............................................. 9827186

(51) Int. Cl.⁷ ......................... G01K 13/02; G01K 1/00
(52) U.S. Cl. ..................... 374/135; 374/109; 374/138; 165/11.1
(58) Field of Search .............................. 374/109, 135, 374/138; 236/DIG. 19; 126/563, 585; 165/11.1, 128, 142

(56) References Cited

U.S. PATENT DOCUMENTS

| 2,900,821 A | * | 8/1959 | Rich ........................... 374/138 |
| 3,664,193 A | * | 5/1972 | Nielsen ....................... 374/109 |
| 3,933,043 A | | 1/1976 | Shuler |
| 3,940,988 A | | 3/1976 | Reed |
| 4,162,473 A | * | 7/1979 | Utasi ............................. 367/99 |
| 4,352,290 A | * | 10/1982 | Neils ........................... 374/110 |
| 4,516,565 A | * | 5/1985 | Stone .......................... 126/585 |
| 4,621,615 A | * | 11/1986 | McGee ........................ 126/572 |
| 4,672,845 A | * | 6/1987 | Hirsch et al. .................. 73/151 |
| 5,008,775 A | * | 4/1991 | Schindler et al. ........... 361/681 |

FOREIGN PATENT DOCUMENTS

| GB | 0734702 | | 8/1955 |
| GB | 2175693 A | | 12/1986 |
| JP | 09288012 | * | 11/1997 |

\* cited by examiner

*Primary Examiner*—Diego Gutierrez
*Assistant Examiner*—Lydia M. De Jesús
(74) *Attorney, Agent, or Firm*—Nixon & Vanderhye P.C.

(57) ABSTRACT

The sensor has an outer member 10 formed with an upwardly directed hole 12 having an open upper end 14. An inner member in the form of a tube 16 is provided having a lower portion 18 positioned in the hole 12 and an upper portion 19 which projects above the outer member 10. Solar radiation applied to the upper portion 19 of the tube 16 creates a chimney effect which causes air to flow upwardly inside the tube 16 and downwardly from the open upper end 14 through a space 22 between the inner and outer members 10, 16. Sensing devices 24, 26 for sensing temperature and humidity are arranged within the outer member 10 and in the air flow path.

14 Claims, 1 Drawing Sheet

AMBIENT AIR TEMPERATURE AND/OR HUMIDITY SENSOR

BACKGROUND OF THE INVENTION

1. Field of the Invention

The invention relates to a sensor and is primarily concerned with a sensor for sensing temperature and/or humidity of ambient air.

2. Discussion of Prior Art

One of the problems with sensors used to sense temperature and/or humidity is that of maintaining accuracy in the presence of strong sunlight. It is known to install sensing devices in ventilated housings such as a Stevenson Screen which are coloured white to minimise the effect of sunlight. However, white makes the sensor highly visible which is not always desirable.

When measuring temperature and/or humidity, a flow of air over the sensing device should ideally be provided. In the Stevenson Screen, air flows through the ventilated housing but relies on a slight wind to achieve that. With no significant air movement on a sunny day, the temperature of the interior of the housing can rise giving an inaccurate record of ambient temperature. Whilst it has been proposed to utilise a powered fan to provide a flow of air over a sensing device to reduce that problem, the use of a fan is undesirable in dust and sand environments and can become noisy and unreliable.

SUMMARY OF THE INVENTION

An object of the present invention is to provide an improved sensor which will help to overcome the above problems.

According to the invention there is provided a sensor comprising a tube having a first portion and a second portion, a shielding member having a cavity therein, and at least one sensing device for sensing a characteristic of ambient air, wherein the first portion of the tube is positioned within the cavity of the shielding member and the second portion of the tube is arranged to protrude from the cavity, there being a clearance between the outer surface of the first portion of the tube and the surface of the shielding member surrounding the cavity such that heat applied to the first portion of the tube causes air to flow through the tube in a direction from the first portion towards the second portion thereby drawing fresh air into the cavity through the clearance between the tube and the shielding member and wherein the sensing device is located within the cavity of the shielding member.

The tube produces a chimney effect as the second portion heats up as a result of, say, solar radiation, causing the air to flow even in the absence of a light wind. Moreover, as the sensing device is arranged within the shielding member it is shielded from direct sunlight.

The sensing device may be arranged on the first portion of the tube and is preferably arranged on the inside of the first portion of the tube. In that way, the sensing device is particularly well shielded from direct sunlight.

Preferably, the cavity has a closed lower end.

The lower portion of the tube has a first end arranged adjacent the closed end of the cavity.

Although the downward flow of air between the tube and shielding member will help to insulate the sensing device from solar radiation where the sensing device is arranged on the tube, it is desirable to produce the shielding member from an insulative material such as plastics so that the shielding member does not readily heat up and radiate heat across the clearance space to the sensing device.

Preferably, the tube is made from a relatively heat conductive material, most preferably the material is at least partly metallic.

Optionally, the tube may be fluted to provide maximum heat transfer.

The sensing device preferably senses meteorological air characteristics such as temperature or humidity.

If desired, a plurality of sensing devices can be provided. For example, two sensors may be provided for sensing temperature and humidity respectively.

In a preferred embodiment, the cavity and the tube are arranged to be substantially coaxial and preferably define an annular space between them.

BRIEF DESCRIPTION OF THE DRAWINGS

A sensor in accordance with the invention will now be described by way of example with reference to the accompanying drawings in which.

DETAILED DISCUSSION OF PREFERRED EMBODIMENTS

Figure 1:
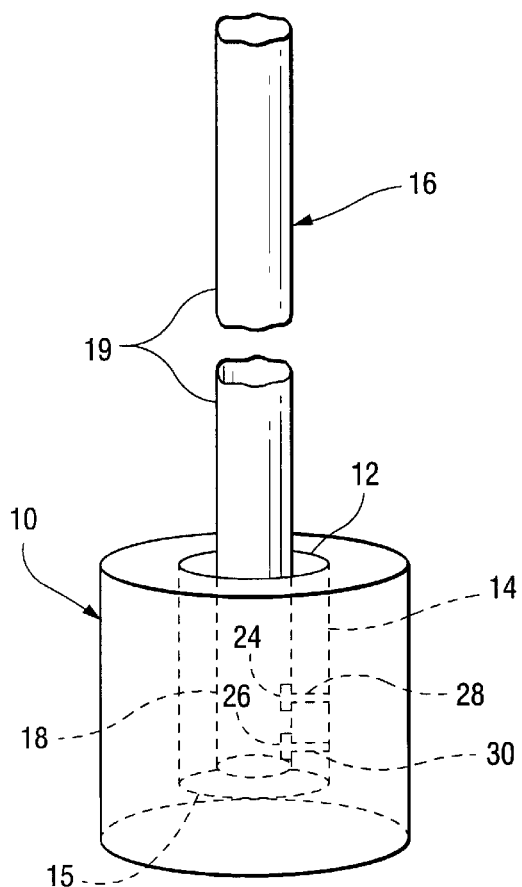
FIG. 1 is a diagrammatic perspective view of a sensor in accordance with the invention and FIG. 2 is a vertical cross section through the sensor shown in FIG. 1.

The sensor comprises a pot-like outer member 10 made of heat insulative material such as a plastic. The outer member 10 has therein a vertical hole 12 which has an opening 14 at its upper end and a closed lower end 15 as viewed in the drawings. An elongate inner member in the form of a thin-walled tube 16 is provided which has a lower portion 18 positioned in the hole 12 and an upper portion 19 which projects out of the opening 14 and extends above the outer member 10.

The bottom of the lower portion 18 is spaced from the closed lower end 15 of the hole 12. As will be appreciated from the drawings, the outer member 10 has a wall 20 which is considerably thicker than the wall of the tube 16, the tube wall being indicated at 21. At least the upper portion 19 of the tube 16 is metallic, e.g. made of aluminium. The hole 12 and the tube 16 are of circular transverse cross-section and are substantially coaxial so as to define an annular clearance space 22 between them.

Figure 2:
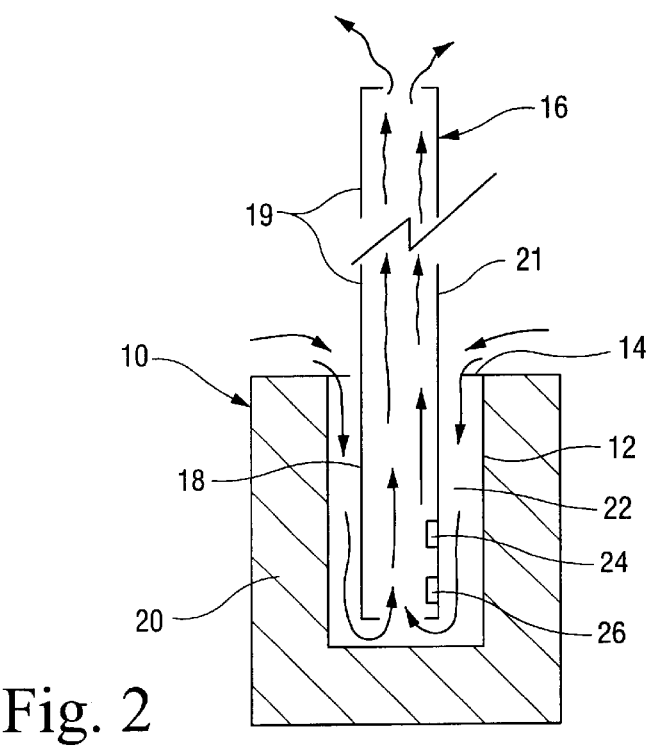

The lower portion 18 of the tube 16 has two sensing devices 24, 26 mounted on the inside of its wall 21 as shown in FIG. 2. In the particular embodiment shown, the sensing device 24 is a temperature sensor and the sensing device 26 is a humidity sensor. It will be noted that the sensing devices 24, 26 are placed towards the bottom end of the lower portion 18 of the tube 16. Signals from the sensing devices 24, 26 are transmitted through respective wires 28, 30 to monitoring circuitry (not shown).

In use, the sensor is positioned at a suitable location where, say, temperature and humidity are to be monitored. When subjected to solar radiation, the upper portion 19 of the tube 16 above warms up and the warmed air inside it rises creating a chimney effect in the tube 16. As indicated by arrows in FIG. 2 the rising air in the tube 16 draws fresh ambient air into the bottom of the lower portion 19, the incoming air flowing downwardly through the annular space 22 from the open upper end 14 of the hole 12 in the outer member 10. Although the outer member 10 may also be subject to solar radiation, the relatively thicker wall 20 and the fact that the outer member is formed from an insulative material shields the sensing devices 24, 26 from heat resulting from such solar radiation. Also, additional insulation is provided by the flow of ambient air downwards through the annular space 22.

The air flows over the sensing devices 24, 26 arranged in the air flow path and enables the them to provide accurate readings from the air flowing up the inside of the tube 16. There is minimal risk of inaccuracies arising resulting from the superimposition of heat due to direct solar radiation on the outer member 10. Also with both the upper open end 14 of the outer member 10 and the upper open end of the tube 16 facing the same way, a form of balanced flue is achieved which helps to prevent the effect of wind creating undesirable air flow problems.

Whereas in the prior art, solar radiation is a significant problem, the present invention uses solar radiation to advantage to improve the accuracy the sensing device. As will be appreciated, the construction of the sensor is straightforward making it simple and relatively inexpensive to manufacture particularly when compared to sensors requiring the presence of a fan to create a flow of air.

What is claimed is:

1. A sensor comprising: a tube having a first portion and a second portion, a shielding member having a cavity therein, and at least one sensing device for sensing a characteristic of ambient air, wherein the first portion of the tube is positioned within the cavity of the shielding member and the second portion of the tube is arranged to protrude from the cavity, there being a clearance between the outer surface of the first portion of the tube and the surface of the shielding member surrounding the cavity such that heat applied to the first portion of the tube causes air to flow through the tube in a direction from the first portion towards the second portion thereby drawing fresh air into the cavity through the clearance between the tube and the shielding member and wherein the sensing device is located within the cavity of the shielding member.

2. A sensor according to claim 1 in which the sensing device is arranged on the first portion of the tube.

3. A sensor according to claim 1 in which the sensing device is arranged on the inside of the first portion of the tube.

4. A sensor according to claim 1 in which the cavity in the shielding member has a closed lower end.

5. A sensor according to claim 1 in which the first portion of the tube has a first end arranged adjacent the closed end of the cavity.

6. A sensor according to claim 1 in which the shielding member is made from an insulative material.

7. A sensor according to claim 1 in which the tube is made from a conductive material.

8. A sensor according to claim 7 in which the tube is comprised at least partially of a metallic material.

9. A sensor according to claim 1 wherein the tube is fluted.

10. A sensor according to claim 1 comprising a sensing device which senses temperature.

11. A sensor according to claim 1 comprising a sensing device which senses humidity.

12. A sensor according to claim 1 in which the tube and the cavity are arranged to be substantially coaxial.

13. A sensor according to claim 1 in which the cavity is hole of circular transverse cross section.

14. A sensor according to claim 1 in which the tube is of circular transverse cross section.

* * * * *

UNITED STATES PATENT AND TRADEMARK OFFICE
CERTIFICATE OF CORRECTION

PATENT NO. : 6,406,180 B1
DATED : June 18, 2002
INVENTOR(S) : Walker et al

It is certified that error appears in the above-identified patent and that said Letters Patent is hereby corrected as shown below:

<u>Column 1,</u>
Line 44, "first" should read -- second --.

<u>Column 4,</u>
Line 1, "first" should read -- second --.

Signed and Sealed this

Fourth Day of March, 2003

JAMES E. ROGAN
*Director of the United States Patent and Trademark Office*